United States Patent
Kirniak

(10) Patent No.: US 9,872,963 B2
(45) Date of Patent: Jan. 23, 2018

(54) DEVICE FOR DISPENSING A FLUID PRODUCT

(75) Inventor: Maxime Kirniak, Rouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 1013 days.

(21) Appl. No.: 13/808,479

(22) PCT Filed: Jul. 5, 2011

(86) PCT No.: PCT/FR2011/051576
§ 371 (c)(1),
(2), (4) Date: Feb. 25, 2013

(87) PCT Pub. No.: WO2012/004509
PCT Pub. Date: Jan. 12, 2012

(65) Prior Publication Data
US 2013/0152928 A1 Jun. 20, 2013

(30) Foreign Application Priority Data
Jul. 7, 2010 (FR) ..................................... 10 55527

(51) Int. Cl.
*A61M 15/00* (2006.01)

(52) U.S. Cl.
CPC ...... *A61M 15/0045* (2013.01); *A61M 15/004* (2014.02); *A61M 15/0008* (2014.02);
(Continued)

(58) Field of Classification Search
CPC ............ A61M 15/00; A61M 15/0001–15/001; A61M 15/0013–15/0026;
(Continued)

(56) References Cited

U.S. PATENT DOCUMENTS

2009/0308389 A1* 12/2009 Pocock et al. ........... 128/203.15
2010/0258120 A1    10/2010 Colomb

FOREIGN PATENT DOCUMENTS

WO    2008/012456 A2    1/2008
WO    2009/077697 A1    6/2009

* cited by examiner

*Primary Examiner* — Todd J Scherbel
*Assistant Examiner* — Ned T Heffner
(74) *Attorney, Agent, or Firm* — Sughrue Mion, PLLC

(57) ABSTRACT

A fluid dispenser, including a cover element; a blister strip; a blister opening mechanism; a first displacement mechanism having an indexer wheel; a second displacement mechanism pivoting between a non-dispensing position and a dispensing position; a cocking member for urging the second displacement mechanism towards the dispensing position, the cocking member spring-loaded by opening the cover; a blocking mechanism for retaining the second displacement mechanism in the non-dispensing position; a trigger mechanism for releasing the blocking mechanism; a slidable carriage displaceable between a non-indexing position and an indexing position and including an actuator co-operating with the indexer wheel; a connection mechanism activated during inhalation that connects the carriage with the cover, so as to displace said carriage towards its indexing position when the cover element is brought towards its closed position, and so as to displace said carriage towards its non-indexing position when brought towards its open position.

8 Claims, 3 Drawing Sheets

(52) U.S. Cl.
CPC .... *A61M 15/0026* (2014.02); *A61M 15/0033* (2014.02); *A61M 15/0041* (2014.02); *A61M 15/0051* (2014.02); *A61M 15/0055* (2014.02); *A61M 15/0091* (2013.01); *A61M 15/0096* (2014.02); *A61M 15/0073* (2014.02); *A61M 15/0075* (2014.02); *A61M 15/0078* (2014.02); *A61M 2202/064* (2013.01)

(58) Field of Classification Search
CPC ............... A61M 15/0028–15/0038; A61M 15/004–15/0043; A61M 15/0045–15/0051; A61M 15/0056; A61M 15/006; A61M 15/0065; A61M 15/0068–15/0083; A61M 15/0086–15/0088; A61M 15/0091–15/0098; A61M 15/06; A61M 15/08–15/085; A61M 2202/064; A61J 1/2006–1/2017; A61K 9/14; G06M 1/00
See application file for complete search history.

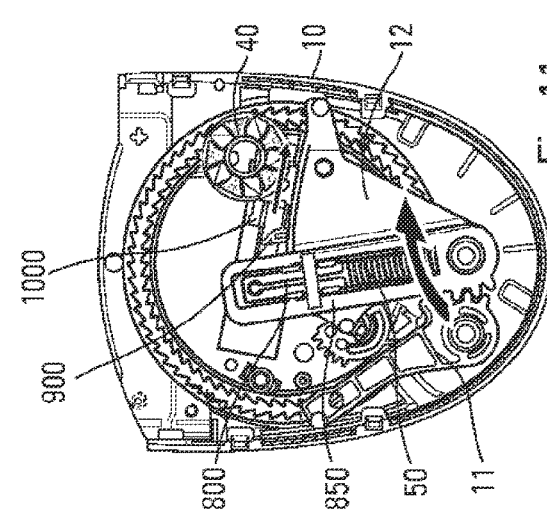
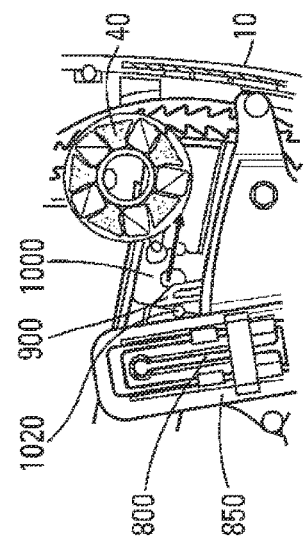
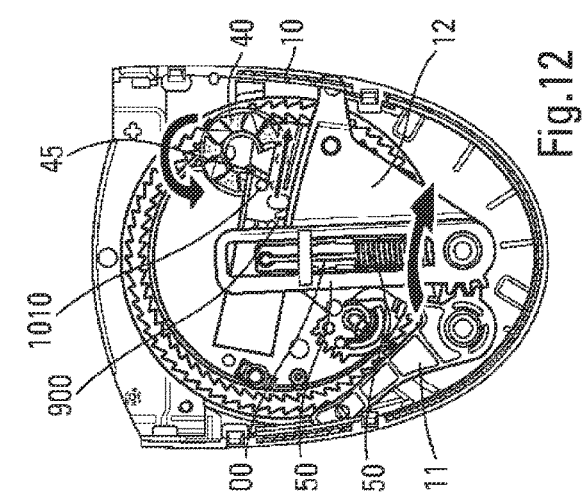
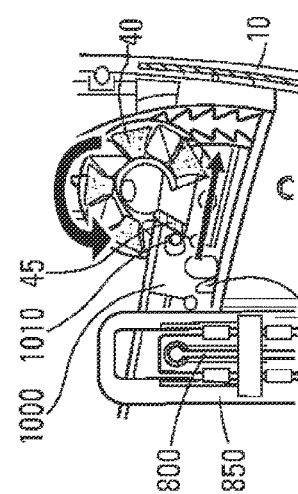
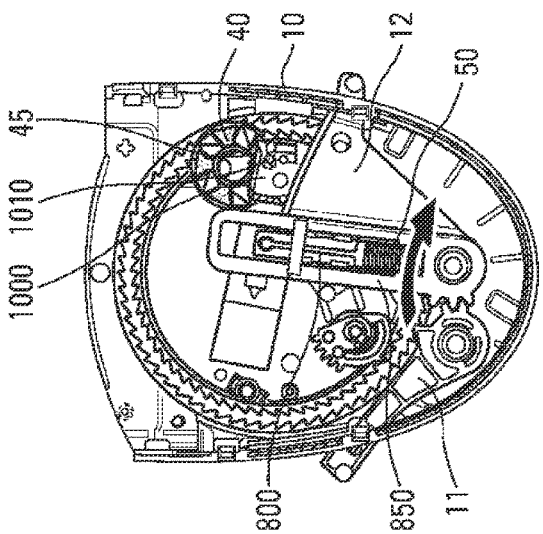
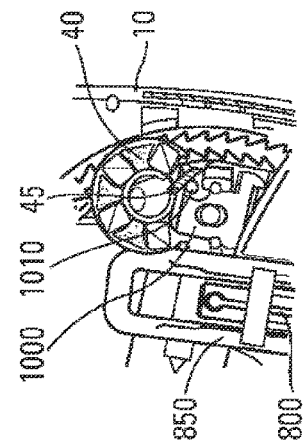

DEVICE FOR DISPENSING A FLUID PRODUCT

CROSS REFERENCE TO RELATED APPLICATIONS

This application is a National Stage of International Application No. PCT/FR2011/051576 filed Jul. 5, 2011, claiming priority based on French Patent Application No. 1055527 filed Jul. 7, 2010, the contents of all of which are incorporated herein by reference in their entirety.

The present invention relates to a fluid dispenser device, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in placing the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of metering accuracy and reproducibility on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the preceding dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. Another problem that exists with inhalers provided with blister strips is associated with the movement of the strip, and with storage of the used portion of the strip. Thus, depending on the length of the strip and/or the thickness of the blisters, a large amount of space can turn out to be necessary, and any blockage of the blister strip can prevent the inhaler from functioning properly. In addition, when the device for advancing the strip pulls simultaneously on the leading end of the strip so as to avoid poor rolling up, a problem can occur over successive actuations, in particular because the rolled-up diameter of the used strip increases progressively.

An object of the present invention is to provide a fluid dispenser device, in particular a dry-powder inhaler, that does not have the above-mentioned drawbacks.

In particular, an object of the present invention is to provide such a device that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

The present invention thus provides a fluid dispenser device, comprising:
  a body provided with a dispenser orifice;
  at least one cover element that is movable between a closed position and an open position;
  a plurality of individual blisters each containing a dose of fluid, such as a pharmaceutical powder, said blisters being formed on an elongate blister strip;
  blister opening means for opening a respective full blister each time said opening means are actuated;
  first displacement means for displacing said blister strip so as to bring a full blister to face said opening means before each inhalation, said first displacement means comprising an indexer wheel provided with at least one cavity that receives the blisters;
  second displacement means for displacing said blister strip, said second displacement means pivoting between a non-dispensing position and a dispensing position in which a blister co-operates with said opening means, said indexer wheel being mounted to turn on said second displacement means, such that in the dispensing position, said indexer wheel is displaced against said opening means so as to open the blister arranged in said cavity;
  a cocking member for urging said second displacement means towards said dispensing position, said cocking member being spring-loaded by compressing a spring by opening said at least one cover element;
  blocking means for retaining said second displacement means in the non-dispensing position;
  trigger means for releasing said blocking means and for enabling said second displacement means, and thus said indexer wheel, to be displaced towards said dispensing position, said trigger means being actuated by the user inhaling;
  a slidable carriage that is displaceable between a non-indexing position and an indexing position, said non-indexing position corresponding to the open position of said at least one cover element, and the indexing position corresponding to said closed position of said at least one cover element, said carriage including an actuator member that co-operates with said indexer wheel so at to turn it when said carriage is displaced from its indexing position towards its non-indexing position;

connection means which, when they are activated, connect said carriage with said at least one cover element, so as to displace said carriage towards its indexing position when said at least one cover element is brought from its open position towards its closed position, and so as to displace said carriage towards its non-indexing position when said at least one cover element is brought from its closed position towards its open position; and said connection means being activated while said second displacement means are being displaced towards said dispensing position while the user is inhaling, and being deactivated in the absence of any inhalation, such that opening said at least one movable cover and then closing it without inhaling does not cause said indexer wheel to turn.

Advantageously, said connection means comprise a connection finger that is displaceable together with said cocking member.

Advantageously, said indexer wheel includes a set of teeth that co-operate with the actuator member of said carriage when said carriage is displaced from its indexing position towards its non-indexing position.

Advantageously, the device includes two cover elements that are meshed together.

These characteristics and advantages and others of the present invention appear more clearly from the following detailed description, given by way of non-limiting example, and with reference to the accompanying drawing, and in which:

FIGS. 11 to 13 are views similar to the views in FIGS. 5 and 6, showing an opening cycle of the device after inhalation during the preceding cycle; and FIGS. 14 to 16 show diagrammatic and fragmentary views of FIGS. 11 to 13.

Figure 1:
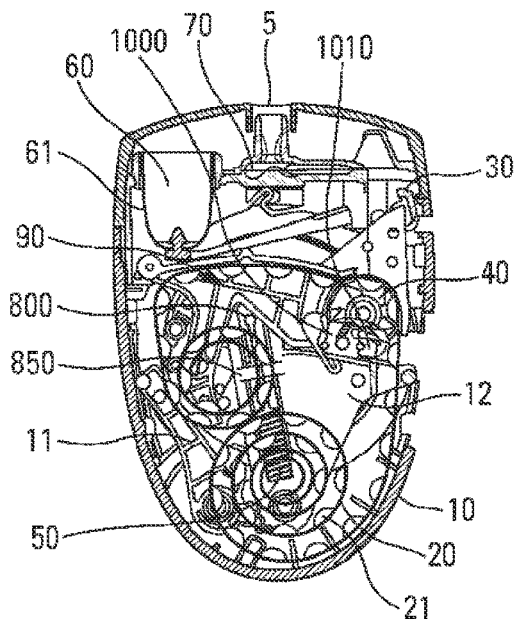
FIGS. 1 to 4 are section views of a dispenser device in an advantageous embodiment of the invention, during an opening then a closing cycle of the device, without the user inhaling in the open position.

The figures show an advantageous embodiment of a dry-powder inhaler. The inhaler includes a body 10 on which there can be slidably mounted two cover-forming portions 11, 12 (shown only in part for the purpose of clarity) that are adapted to be opened so as to open and spring-load the device. The body 10 can be approximately rounded in shape, as shown in the figures, but it could be of any other appropriate shape. The body 10 includes a mouthpiece or inhaler endpiece 5 that defines a dispenser orifice through which the user inhales while the device is being actuated. The orifice is typically arranged approximately at the center of the top portion (in the position shown in the drawings). The covers 11, 12 can open by pivoting about a common pivot axis, or about two parallel axes by being meshed together. Any other opening means for opening the device can be envisaged. In a variant, the device could include only a single cover instead of two.

Inside the body 10 there is provided a strip of individual reservoirs 21, also known as blisters, said strip being made in the form of an elongate strip 20 on which the blisters 21 are disposed one behind another, in manner known per se. The blister strip is advantageously constituted by a base layer or wall that forms the cavities receiving the doses of powder, and by a closure layer or wall that covers each of said blisters in sealed manner. Before first use, the blister strip can be rolled-up inside the body 10, preferably in a storage portion, and first strip displacement means 40, in particular rotary means, are provided for progressively unrolling the blister strip and for causing it to advance. Second displacement means, in particular means that are mounted to pivot on the body 10, are provided for bringing a respective blister into a dispensing position each time the device is actuated. The second displacement means are mounted to pivot between a non-dispensing position and a dispensing position in which a blister co-operates with said opening means. The strip portion including the empty blisters is advantageously adapted to be rolled-up at another location of said body 10, preferably a reception portion, as described in greater detail below.

The inhaler includes blister opening means (not shown for the purpose of clarity) preferably comprising a perforator and/or cutter needle for perforating and/or cutting the closure layer of the blisters. For example, the opening means comprise a needle that is stationary relative to the body 10, and against which a respective blister is displaced on each actuation by the second displacement means. The blister is thus perforated by said needle, which penetrates into said blister so as to expel the powder by means of the suction of the user inhaling.

The first displacement means 40 are adapted to cause the blister strip to advance after each inhalation of the user. The second displacement means are adapted to displace the blister to be emptied against said opening means during actuation, before each inhalation. The second displacement means can be urged by a resilient element, such as a spring or any other equivalent resilient element, said resilient element being suitable for being prestressed while the device is being opened. Preferably, the first displacement means are formed by an indexer wheel 40 that receives and guides the blister strip. The description below is thus made with reference to such an indexer wheel. Turning the indexer wheel 40 causes the blister strip to advance. Before each inhalation, a full blister is always in a position facing the opening means. The second displacement means can include a pivot member that is mounted to pivot about a pivot axis, said indexer wheel 40 being rotatably mounted on said pivot member.

An actuation cycle of the device can be as follows. During opening of the device, the two cover-forming lateral portions 11, 12 are moved away from each other by pivoting about the body so as to open the device and thus spring-load the device. In this position, the indexer wheel 40 cannot be displaced towards the needle, since the second displacement means are held by appropriate blocking means 30. While the user is inhaling through the mouthpiece, the blocking means are unblocked, thereby causing said indexer wheel 40 to move towards the needle, and thereby causing a blister to be opened.

Preferably, the blister 21 is displaced towards its opening position in order to be opened by the needle that is stationary relative to the body 10. However, it can be envisaged that the needle could also be movable during the stage of opening the blister. For example, the needle could be displaced towards the blister while the blister is being displaced towards the needle. In another variant, it is also possible to envisage that the blister and the needle are displaced in the same direction during actuation, the blister being displaced more quickly in said direction, such that it comes into contact with the needle so as to be opened.

As explained above, it is desirable for the opening means to be actuated by the user inhaling. In order to trigger the opening means by inhalation, an inhalation trigger system is provided that advantageously comprises a unit 60 that is displaceable and/or deformable under the effect of inhalation, the unit being adapted to release the blocking means. The unit advantageously comprises a deformable diaphragm or air-chamber 61. Inhalation by the user causes said deformable air-chamber to deform, thereby making it possible to release said blocking means and to enable the second displacement means to be displaced, and therefore to enable a respective blister to be displaced towards its opening position. The blister is therefore opened only on inhalation, such that it is emptied simultaneously. Thus, there is no risk of any of the dose being lost between opening the blister and emptying it.

In a variant, other inhalation trigger means could also be used, e.g. using a pivotable valve flap that, while the user is inhaling, pivots under the effect of the suction created by the inhalation, with pivoting of the valve flap causing the blocking means to be released, thereby causing the blister to be displaced towards the opening means.

The inhaler further includes a dispenser or dispersion chamber 70 for receiving the dose of powder after a respective blister has been opened. The dispenser chamber is advantageously provided with at least one and preferably more beads that are displaced inside said chamber during inhalation so as to improve dispensing of the air and powder mixture after a blister has been opened, in order to increase the effectiveness of the device.

It can be advantageous for the opening means, in particular the needle, to be formed directly on said dispenser chamber, e.g. at the end of a channel leading to said chamber.

After inhalation, when the user closes the device, all of the components return to their initial, rest positions. The device is thus ready for a new utilization cycle.

In an advantageous aspect of the inhaler, the blisters are formed on a flexible elongate strip that, initially, is mainly stored in the form of a roll in a storage housing inside the body 10 of the device. Advantageously, the rolled-up blister strip is held by inner walls of said storage housing without its rear end (rear in the advancement direction of the blister strip) being fastened relative to said body 10, thereby enabling the blister-strip roll to be assembled more easily inside the device. The blister strip is displaced by means of the indexer wheel 40 that advantageously presents at least one and preferably more recesses, each having a shape that corresponds to the shape of the blisters. Thus, when the indexer wheel 40 turns, it causes the blister strip to advance. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of sprocket wheels co-operating with said holes.

After opening one or more blisters, the blister-strip portion with the empty blisters must be suitable for being stored in easy and compact manner in the device, while avoiding any risk of blockage. Advantageously, the used blister strip is rolled-up automatically, once again forming a roll.

In still another aspect of the inhaler, a dose counter or indicator device (not shown) is also provided. The device may include numbers or symbols that are marked directly on the blister strip, and that are visible through an appropriate window in the body 10 of the device. In a variant, it is possible to envisage using one or more rotary disks or rings including numbers or symbols.

FIGS. 1 to 4 show an opening and closing cycle of the device, without the user inhaling in the open position. The displacements of certain parts are indicated diagrammatically by arrows in these figures.

Figure 3:
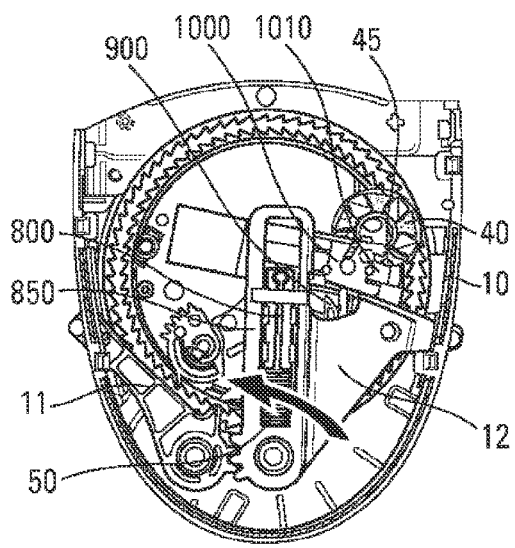
Figure 4:
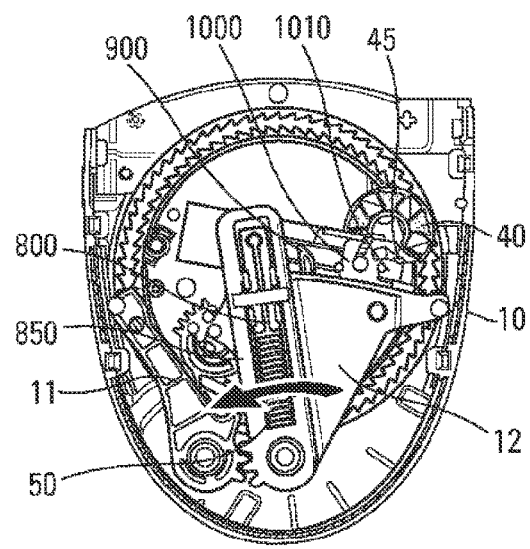

The movable cover element 12 supports a cocking member 800, advantageously made in the form of a rod that can slide in a housing 850 that is secured to said cover element 12. The cocking member 800 thus pivots relative to said body 10 together with the cover element 12. The cocking member 800 may be moved against a spring 50, advantageously a coil spring, that is arranged in said housing 850. The cocking member 800 is thus connected at one end to said spring 50, and at the other end it co-operates with the second displacement means, in particular with a pivot member 90 that is mounted to pivot on the body 10, and on which the indexer wheel 40 is fastened is rotary manner. When the movable cover element 12 is opened, as shown in FIG. 1 (closed position) and in FIG. 2 (open position), the cocking member 800 is displaced in its housing 850 by compressing the spring 50. The pivot member 90 of the second displacement means is itself prevented from moving by the blocking means 30 that are released only at the moment of inhalation. Thus, in the absence of any inhalation in the open position in FIG. 2, closing the cover elements merely causes the cocking member 800 to return to its rest position and the spring 50 to decompress. This is shown in FIGS. 3 and 4. In its portion in contact with the pivot member, the rod 800 advantageously includes a rounded portion, such as a ball-shaped end, to encourage the rod 800 to slide over the part with which it co-operates.

Figure 2:
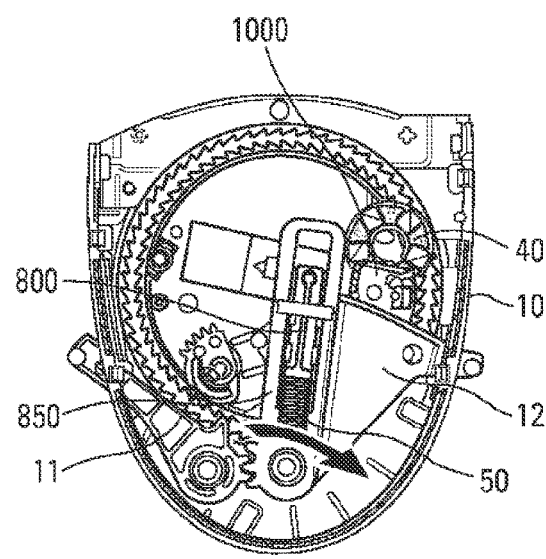

Thus, by opening the inhaler, the user spring-loads the system (FIGS. 1 and 2). If the user does not inhale and closes the inhaler, said inhaler merely returns to its start position without displacing the blister strip or the blocking means (FIGS. 3 and 4). There is thus no risk of a blister (and thus an active dose of substance) being lost by accidental or incomplete actuation in which the user does not inhale between opening and closing. Opening the blister, emptying it, dispensing the powder into the lungs of the user, displacing the blister strip to bring a new full blister to face the opening means, and counting the dose are thus possible only if the user inhales.

Figure 5:
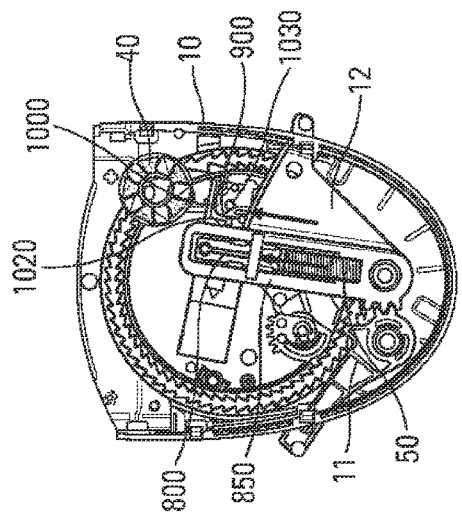
FIGS. 5 to 10 show similar views to the views in FIG. 1, during an opening then a closing cycle of the device, with the user inhaling in the open position.
Figure 6:
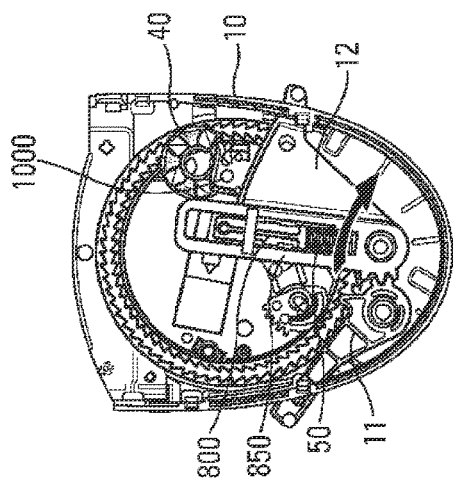
Figure 7:
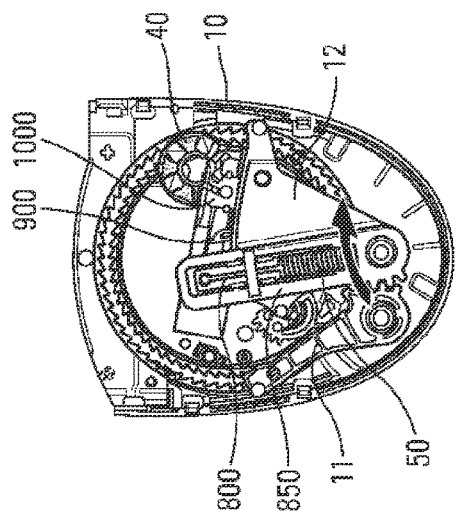

The blocking means 30 that block the second displacement means, and in particular the pivot member that co-operates with the cocking member 800, are connected to the deformable diaphragm 61 that is sensitive to the inhalation of the user, such that while the user is inhaling, said diaphragm deforms, thereby releasing said blocking means. This enables said second displacement means to be displaced towards their dispensing position under the effect of the force exerted by the compressed spring 50. Such displacement causes a full blister to be opened and a dose to be dispensed. FIGS. 5 to 7 show the opening of the device followed by inhalation.

Figure 8:
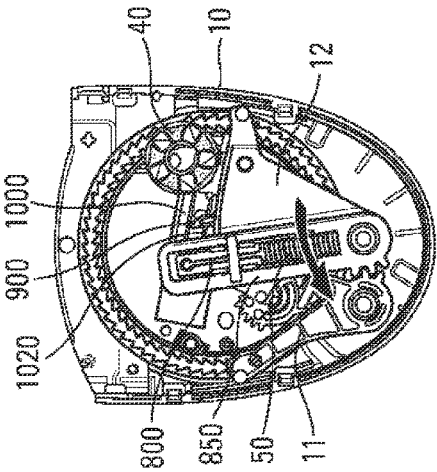
Figure 9:
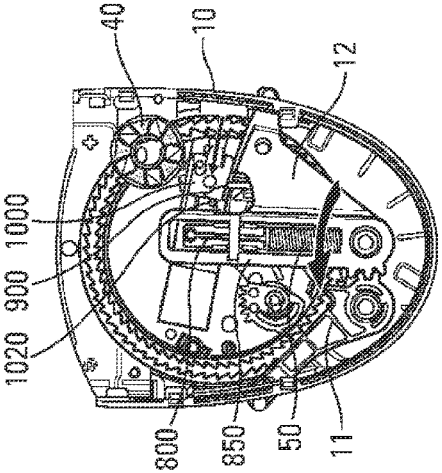
Figure 10:
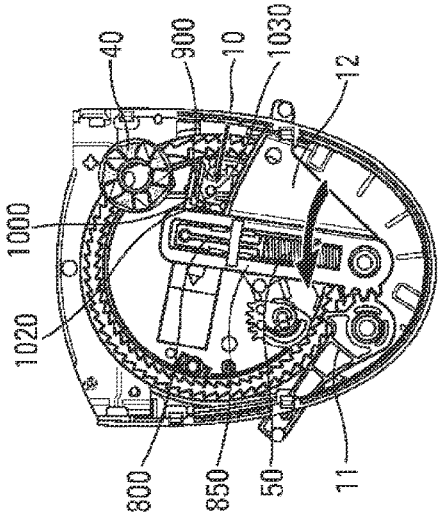

In order to turn the indexer wheel 40, and thus advance the blister strip and bring the next blister to face the needle of the opening means, the device includes a slidable carriage 1000. The carriage may slide approximately transversally or horizontally in the position of the device in the figures. A connection finger 900 is associated with the cocking member 800 and is displaced with it. Thus, when the cocking member 800 slides in its housing 850 by compressing the spring 50 during opening of the device, said connection finger 900 also slides in the same direction. In the open position, the connection finger 900 does not co-operate with said carriage 1000 so long as the user has not inhaled. Thus, if the user does not inhale after opening the cover elements, and if the user then closes said cover elements, the connection finger is not connected with said carriage, and said carriage is not displaced by the opening, then the closing, of said cover elements. It is only when the user inhales in the open position (FIGS. 6 and 7) that said connection finger 900 is displaced, together with said cocking member 800, under the effect of the spring 50, so as to mesh with said carriage 1000, or so as to co-operate therewith in some other way. In the embodiment shown, the connection finger 900 is inserted between two lateral projections 1020, 1030 of said carriage 1000 as can be seen in FIG. 7 in particular. Thus, after inhalation, the finger 900 is in a connected position in which it is connected with said carriage 1000. When the user closes the cover elements once again after inhaling, as shown in FIGS. 8 to 10, said cover element 12 that supports the cocking member 800 and the connection finger 900, pivots towards the left in the figures, as represented by the thick curved arrows. The connection finger 900, by following this pivoting movement, causes the carriage 1000 to slide towards the left in the figures, as shown by the small straight arrows in FIGS. 8 and 9. Simultaneously, during such closure, said second displacement means also return to their non-actuated position, returning the indexer wheel 40 away from the needle of the opening means. Whereas said indexer wheel 40 does not co-operate with said carriage 1000 while it is in the actuated position, when it is in the rest or non-actuated position, a set of teeth 45 of said indexer wheel lie in the path of an actuator portion 1010 of said carriage 1000. Thus, when the user opens the cover elements once again after a preceding cycle with inhalation, i.e. starting from the position shown in FIGS. 10 and 11, said connection finger 900 returns the carriage 1000 towards the right in the figures, towards its start position, and this is represented by the small straight arrows in FIGS. 11 and 12. During such sliding towards the right, said carriage 1000 co-operates with the set of teeth 45 of the indexer wheel, thereby causing said wheel to turn so as to advance the blister strip and bring the next blister to face the needle for the next inhalation. FIGS. 14 to 16 show, in more detailed manner, the co-operation between the actuator member 1010 of the carriage and the set of teeth 45 of the indexer wheel. Simultaneously, during such opening, the cocking member 800 is once again spring-loaded, and the connection finger 900 is thus once again disconnected from said carriage 1000 at the end of opening. Thus, if the user closes without inhaling, the carriage 1000 does not move, and the indexer wheel 40 does not turn any more during the next opening. It is only after the next inhalation that the connection finger 900 will be connected once again with the carriage 1000, enabling a new indexing cycle.

An object of the invention is to avoid counting doses that have not been dispensed, e.g. in the event of a manipulation error, or of an incomplete manipulation of the device. It is thus desirable that the counter or indicator is actuated only once the user has inhaled, since it is this inhalation that makes it possible for the blister to open and the dose contained therein to be dispensed. Advantageously, the counter is thus actuated after inhalation, when the user closes the device.

In all of the embodiments described above, the blister strip is formed by a strip presenting two ends. In a variant, it is possible to use a continuous strip. Other modifications are also possible without going beyond the ambit of the present invention.

The present invention therefore makes it possible to provide a dry-powder inhaler that provides the following features:

- a plurality of individual doses of powder stored in individual sealed blisters, e.g. 30 or 60 doses stored on a rolled-up strip;
- the powder is released by perforation that is achieved by the user inhaling, the blister being perforated by means of an inhalation detector system that is coupled to a pre-stressed release system;
- appropriately-shaped drive means that are engaged with blisters so as to displace the blister strip after each inhalation, and bring a new full blister into a position in which it is to be opened by appropriate opening means;
- means for avoiding doses being lost in the event of the inhaler being opened, but in the absence of any inhalation; and
- a dose indicator adapted to count the doses only in the event of inhalation.

Other features are also provided by the device of the invention as described above. It should be observed that the various features, even if they are shown as being provided simultaneously on the inhaler, could be implemented separately. In particular, the inhalation trigger mechanism could be used regardless of the type of reservoir opening means, regardless of the use of a dose indicator, regardless of the way in which the individual blisters are arranged relative to one another, etc. The cocking means and the inhalation trigger system could be made in some other way. The same applies for other component parts of the device.

Various modifications may also be envisaged by a person skilled in the art, without going beyond the ambit of the present invention, as defined by the accompanying claims. In particular, the various characteristics and functions of the device described with reference to the drawings can be combined together in any appropriate manner.

The invention claimed is:

1. A fluid dispenser device, comprising:
    a body provided with a dispenser orifice;
    at least one cover element that is movable between a closed position and an open position;
    a plurality of individual blisters each containing a dose of fluid, said blisters being formed on an elongate blister strip;
    blister opening means for opening a respective full blister each time said opening means are actuated;
    first displacement means for displacing said blister strip in a first direction so as to bring a full blister to face said opening means before each inhalation, said first displacement means comprising an indexer wheel provided with at least one cavity that receives the blisters;
    second displacement means for displacing said blister strip in a second direction, said second displacement means pivoting between a non-dispensing position and a dispensing position in which a blister co-operates with said opening means, said indexer wheel being mounted to turn on said second displacement means, such that in the dispensing position, said indexer wheel is displaced against said opening means so as to open the blister arranged in said cavity;

a cocking member for urging said second displacement means towards said dispensing position, said cocking member being spring-loaded by compressing a spring by opening said at least one cover element;

blocking means for retaining said second displacement means in the non-dispensing position;

trigger means for releasing said blocking means and for enabling said second displacement means, and thus said indexer wheel, to be displaced towards said dispensing position, said trigger means being actuated by a user inhaling;

a slidable carriage that is slidably displaceable along a straight path in a direction traverse to said second direction between a non-indexing position and an indexing position, said non-indexing position corresponding to the open position of said at least one cover element, and the indexing position corresponding to said closed position of said at least one cover element, said carriage including an actuator member that co-operates with said indexer wheel so at to turn the indexer wheel when said carriage is displaced from the indexing position towards the non-indexing position;

connection means which, when activated, connect said carriage with said at least one cover element, so as to displace said carriage towards the indexing position when said at least one cover element is brought from the open position towards the closed position, and so as to displace said carriage towards the non-indexing position when said at least one cover element is brought from the closed position towards the open position; and said connection means being activated while said second displacement means are being displaced towards said dispensing position while the user is inhaling, and being deactivated in the absence of any inhalation, such that opening said at least one movable cover and then closing it without inhaling does not cause said indexer wheel to turn.

2. A device according to claim 1, wherein said connection means comprise a connection finger that is displaceable together with said cocking member.

3. A device according to claim 1, wherein said indexer wheel includes a set of teeth that co-operate with the actuator member of said carriage when said carriage is displaced from the indexing position towards the non-indexing position.

4. A device according to claim 1, including two cover elements that are meshed together.

5. The device according to claim 1, wherein said dose of fluid is a pharmaceutical powder.

6. An inhalation fluid dispenser device, comprising:
a body provided with a dispenser orifice;
a cover element movable between a closed position and an open position;
a plurality of individual blisters, each blister containing an inhalable dose, the blisters formed on an elongated blister strip;
a perforator or cutter that opens each blister in turn;
an indexer wheel that displaces a portion of the blister strip engaged with the indexer wheel so as to bring a full blister from the blister strip to the perforator or cutter before each inhalation;
a displacement arm that displaces the blister strip in a first direction, the displacement arm pivots between a non-dispensing position and a dispensing position in which the full blister co-operates with the perforator or cutter, and the indexer wheel is mounted to turn on the displacement arm such that in the dispensing position, the indexer wheel is at the perforator or cutter so as to open the full blister;
a cocking member that urges the displacement arm towards the dispensing position, the cocking member being spring-loaded by compressing a spring by opening the cover element;
a blocking member that, until released, retains the displacement arm in the non-dispensing position;
a trigger that releases the blocking member and allows the displacement arm to displace the blister strip and the indexer wheel towards the dispensing position, the trigger actuatable by a user inhaling through the inhalation device;
a slidable carriage that is slidably displaceable as a whole along a straight path in translation in a second direction traverse to the first direction between a non-indexing position and an indexing position, the non-indexing position corresponding to the open position of the cover element, and the indexing position corresponding to the closed position of the cover element, the carriage including an actuator member that co-operates with the indexer wheel so at to turn the indexer wheel when the carriage is displaced from the indexing position towards the non-indexing position;
a connection finger that, when activated, connects the carriage with the cover element, so as to displace the carriage towards the indexing position when the cover element is brought from the open position towards the closed position, and so as to displace the carriage towards the non-indexing position when the cover element is brought from the closed position towards the open position; and
the connection finger is activated while the displacement arm is being displaced towards the dispensing position while the user is inhaling, and is deactivated in the absence of inhalation by the user, such that opening the cover and then closing the cover without the user inhaling does not cause the indexer wheel to turn.

7. The inhalation fluid dispenser device according to claim 6, comprising a mouthpiece that defines a conduit for the flow of the inhalable dose to the user's mouth, the conduit positioned at a top of the dispenser, the displacement arm displaces the blister strip in the first direction primarily vertically towards the top of the dispenser, and the slidable carriage is slidably displaceable in translation primarily horizontally towards a side of the dispenser.

8. The inhalation fluid dispenser device according to claim 6, wherein the slidable carriage slides on a guide surface that extends in the second direction.

* * * * *